United States Patent
Stahl et al.

(10) Patent No.: US 6,625,975 B1
(45) Date of Patent: Sep. 30, 2003

(54) DEVICE AND METHOD FOR DETECTING AMMONIA

(75) Inventors: Roland Stahl, Freiberg (DE); Rainer Strohmaier, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/720,699
(22) PCT Filed: Apr. 26, 2000
(86) PCT No.: PCT/DE00/01297
  § 371 (c)(1), (2), (4) Date: Feb. 28, 2001
(87) PCT Pub. No.: WO00/67015
  PCT Pub. Date: Nov. 9, 2000

(30) Foreign Application Priority Data

Apr. 29, 1999 (DE) .......................................... 199 19 472

(51) Int. Cl.$^7$ ................................................. F01N 3/00
(52) U.S. Cl. ............................ 60/286; 60/274; 60/303; 60/301; 60/295
(58) Field of Search ..................... 60/274, 286, 299, 60/301, 303, 295, 276

(56) References Cited

U.S. PATENT DOCUMENTS

| | | | | |
|---|---|---|---|---|
| 3,599,427 A | * | 8/1971 | Jones et al. ..................... 60/30 |
| 5,116,579 A | * | 5/1992 | Kobayashi et al. .......... 423/212 |
| 5,308,810 A | * | 5/1994 | Voss et al. ............... 423/239.1 |
| 5,357,749 A | * | 10/1994 | Ohsuga et al. ................. 60/286 |
| 5,367,875 A | * | 11/1994 | Aboujaoude et al. .......... 60/286 |
| 5,369,956 A | * | 12/1994 | Daudel et al. ................. 60/286 |
| 5,540,047 A | | 7/1996 | Dahlheim et al. |
| 5,628,186 A | * | 5/1997 | Schmelz ....................... 60/286 |
| 5,809,774 A | * | 9/1998 | Peter-Hoblyn et al. ........ 60/286 |
| 5,809,775 A | * | 9/1998 | Tarabulski et al. ............ 60/286 |
| 5,833,932 A | * | 11/1998 | Schmelz ....................... 60/301 |
| 5,968,464 A | * | 10/1999 | Peter-Hoblyn et al. ..... 423/235 |
| 5,976,475 A | * | 11/1999 | Peter-Hoblyn et al. ..... 423/212 |
| 6,082,102 A | * | 7/2000 | Wissler et al. ................. 60/286 |
| 6,105,365 A | * | 8/2000 | Deeba et al. .................. 60/288 |
| 6,125,629 A | * | 10/2000 | Patchett ....................... 60/286 |
| 6,173,568 B1 | * | 1/2001 | Zurbig et al. ................. 60/286 |
| 6,357,226 B2 | * | 3/2002 | Borland ....................... 60/286 |

FOREIGN PATENT DOCUMENTS

DE     3721572      2/1988
EP     0 800 856    10/1997

* cited by examiner

Primary Examiner—Thomas Denion
Assistant Examiner—Diem Tran
(74) Attorney, Agent, or Firm—Kenyon & Kenyon

(57) ABSTRACT

A device and a method for detecting ammonia, especially for detecting an NH$_3$ slip emission in a catalytic converter arrangement, a gas, especially an exhaust gas of a lean-mixture-driven internal combustion engine, being supplied to an SCR catalytic converter via a first gas supply device, and ammonia being supplied via a second gas supply device. The device includes a first arrangement, especially an oxidation catalytic converter, which prior to the supplying of the gas to the SCR catalytic converter, initially at least substantially oxidizes the oxidizable gas components contained in the gas. Emerging gas from the SCR catalytic converter is analyzed by a second arrangement, especially a gas sensor, with respect to the oxidizable components contained in it. The gas sensor may detect oxidizable gas components, including in a non-selective manner, and is connected via a processing unit and a control unit to a dosing system, which regulates the supply of ammonia.

16 Claims, 1 Drawing Sheet

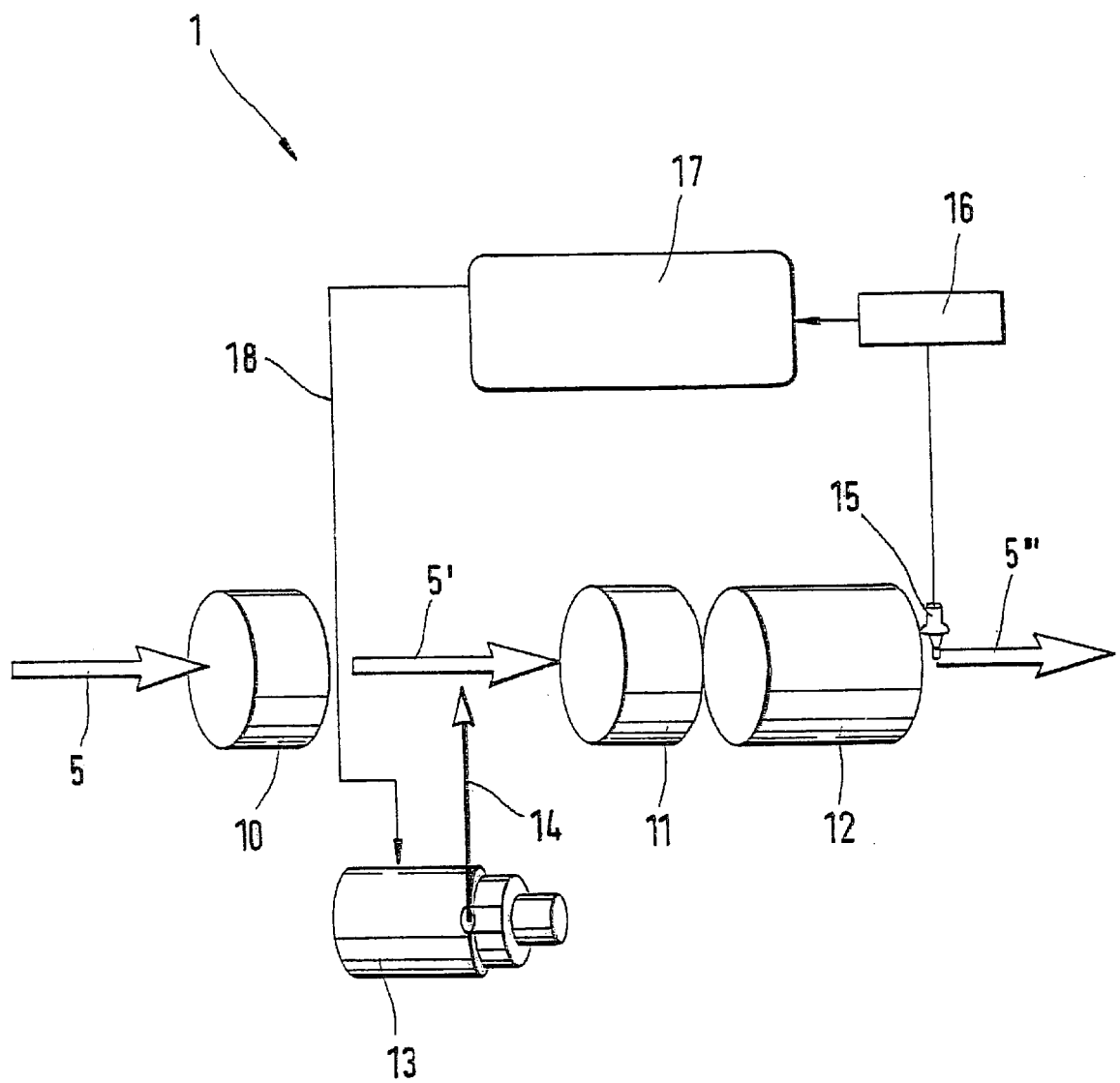

DEVICE AND METHOD FOR DETECTING AMMONIA

FIELD OF THE INFORMATION

The present invention relates to a device and a method for detecting ammonia, especially an $NH_3$ slip, in a catalytic converter arrangement.

BACKGROUND INFORMATION

For reducing the $NO_x$ emissions from lean-mixture-driven internal combustion engines, especially diesel engines, an SCR catalytic converter ("selective catalytic reduction") may be used for the exhaust treatment. In this respect, reference should be made to D. Schöppe, et al., "A Regulated Exhaust Treatment System for Meeting Future Emissions Threshold Values in Diesel Engines," Progress Reports, VDI, Series 12, No. 267, Vol. 1 (1996), 17th International Vienna Engine Symposium, pp. 332–353, in which the mode of operation and the construction of an SCR catalytic converter of this type is discussed.

Summarizing, in an SCR catalytic converter, a selective catalytic reduction of $NO_x$ to $N_2$ takes place, $NH_3$ (ammonia) acting as a reducing agent, which can be obtained from a liquid urea solution in a hydrolysis catalytic converter upstream of the SCR catalytic converter.

However, in the operation of a system of this type for an exhaust treatment using an SCR catalytic converter, the problem arises that too much urea may be apportioned out, so that unconverted ammonia reaches the ambient air along with the exhaust via the SCR catalytic converter. If this $NH_3$ emission is to be suppressed or monitored, an $NH_3$ sensor by be required.

SUMMARY OF THE INVENTION

The exemplary device and method of the present inventions are believed to have the advantage that expensive sensors that specifically target $NH_3$ and that are technically difficult to realize are not used for detecting ammonia or $NH_3$ emissions. As a result, it is possible in an advantageous manner for a broader spectrum of sensor concepts or sensor materials to be considered for use, i e., for detecting ammonia, it is possible to use available gas sensors, especially those that do not react selectively to specific oxidizable gases or gas components, which may represent a significant cost advantage and a simplification with respect to the technology and manufacture of the gas sensors that can be used. In particular, the spectrum of gas sensors that can be used for detecting ammonia can be broadened significantly, in an advantageous manner, to include gas sensors having metallic electrodes, specifically Pt/Au systems, which may already be used as HC sensors.

As a result of the fact that the known SCR catalytic converter, via an upstream first means, has supplied to it an already at least substantially, preferably completely, pre-cleaned or pre-oxidized gas or exhaust gas, this gas already no longer contains any oxidizable or combustible gas components. In particular, gas components HC and CO are no longer contained in this pre-cleaned gas.

Upstream of the feed to the SCR catalytic converter, via a second gas supply device, ammonia is advantageously added to the gas that has been pre-cleaned in this manner, so that in the SCR catalytic converter no oxidizable gas exists apart from $NH_3$. In the event that the totality of the supplied $NH_3$ is not used up in the SCR catalytic converter for reducing the $NO_x$ that is present, an $NH_3$ breakthrough or $NH_3$ emission arises in the SCR catalytic converter, i.e., the gas emerging from the SCR catalytic converter contains ammonia. However, since this ammonia is the only oxidizable gas component contained in the gas, it is not necessary, for detecting the ammonia, to use a means that is specifically targeted to NH3, especially a gas sensor that specifically targets ammonia. A simple sensor suffices that is generally, or across a broad spectrum, sensitive to oxidizable gas components, as is already generally known.

Thus it is believed to be especially advantageous if the gas to be supplied to the SCR catalytic converter before being mixed with ammonia is pre-treated in an available oxidation catalytic converter, which carries out the at least substantial oxidation or pre-cleaning of the gas to be supplied to the SCR catalytic converter.

Supplying the ammonia to the pre-cleaned or pre-oxidized gas, which is to be supplied to the SCR catalytic converter and which, for example, emerges from the oxidation catalytic converter, is carried out in a very advantageous manner using a generally known gas supply device, which includes a hydrolysis catalytic converter for producing ammonia from a chemical compound, especially urea, a dosing system for the dosed and controlled adding of ammonia to the pre-oxidized gas, and an appropriate supply line (e.g., the at least one of the ammonia and the NH3 slip emission is releasable from the at least one of the chemical compound and the urea in the hydrolysis catalytic converter).

Furthermore, it is believed to be advantageous if the second arrangement, device or structure for detecting the oxidizable gas components emerging from the SCR catalytic converter is connected to a processing unit, which is connected via a control unit and a control line to the gas supply device for supplying ammonia to the pre-oxidized gas. In this manner, the addition of ammonia to the gas supplied to the SCR catalytic converter can advantageously be controlled, or, in the form of a closed feedback circuit, can be regulated as a function of the $NH_3$ that is actually consumed for the reduction of $NO_x$, such that the quantity of the unused ammonia emerging from the SCR catalytic converter is minimized or is reduced virtually to zero.

BRIEF DESCRIPTION OF THE DRAWING

The FIGURE shows a block diagram of an exemplary catalytic converter arrangement for detecting an $NH_3$ emission.

DETAILED DESCRIPTION

The FIGURE shows a catalytic converter arrangement 1, such as can be used, for example, in the exhaust gas treatment of diesel engines or of lean-mixture-driven internal combustion engines. Into this catalytic converter arrangement 1 is introduced, initially via an appropriate, an available exhaust gas pipe, a supplied gas 5, in particular a diesel-engine exhaust gas, which has a multiplicity of oxidizable gas components, in particular, for example, HC and CO, as well as nitrogen oxide ($NO_x$). This supplied gas 5 is initially introduced into an available oxidation catalytic converter 10, for example, the one discussed in European Patent Application No. 0800 856, which undertakes a pre-cleaning and pre-oxidation of supplied gas 5, so that the oxidizable gas components contained in supplied gas 5, especially HC or CO, are substantially or completely oxidized or converted, for example, to $H_2O$ or $CO_2$. Thus an at least substantially oxidized gas 5' containing only $NO_x$ as a pollutant component, emerges from oxidation catalytic converter 10.

This at least substantially oxidized gas 5' is then subsequently supplied via a generally known first gas supply device to an SCR catalytic converter 12. However, in this context, it is first provided that, before entering into SCR catalytic converter 12, ammonia is mixed with at least substantially oxidized gas 5'. This takes place using a second gas supply device, which has a dosing system 13, a supply line 14, and a hydrolysis catalytic converter 11. Specifically, for this purpose, dosing system 13 via supply line 14 initially supplies urea to hydrolysis catalytic converter 11, which in a generally known manner is there converted to $NH_3$. This $NH_3$ is then mixed with at least substantially oxidized gas 5' before the gas mixture, generated in this manner, composed of $NH_3$ and at least substantially oxidized gas 5', arrives in SCR catalytic converter 12.

Alternatively, it is also possible, in accordance with the FIGURE, that urea is added in a dosed manner, initially via dosing system 13 and supply line 14, to at least substantially oxidized gas 5', and that this mixture is then supplied to hydrolysis catalytic converter 11, which converts the urea to $NH_3$, so that the gas mixture is composed of at least substantially oxidized gas 5' and $NH_3$.

In this sense, the first gas supply device and the second gas supply device in the exemplary embodiments discussed in accordance with the FIGURE interpenetrate each other and are spatially integrated in each other, because the first gas supply device supplies the generated, at least substantially oxidized gas 5', for example, via appropriate pipes, initially to the second gas supply device, which modifies the gas in hydrolysis catalytic converter 11 as a part of the second gas supply device by adding $NH_3$, and in which thus the at least substantially oxidized gas 5' and the $NH_3$ are mixed together. This gas mixture is then finally supplied to SCR catalytic converter 12.

However, in a further variant of the exemplary embodiment discussed, it is also possible spatially to separate the first gas supply device and the second gas supply device one from the other, so that the first one generates at least substantially oxidized gas 5' and supplies it directly to the SCR catalytic converter, and the second one generates the ammonia and likewise supplies it directly to SCR catalytic converter 12. In this variant, in an advantageous manner, at least substantially oxidized gas 5' and the supplied $NH_3$, before arriving in SCR catalytic converter 12, are additionally mixed using a suitable, an available mixing device.

Finally, in SCR catalytic converter 12, with the assistance of the supplied ammonia in an available manner, the nitrogen oxide ($NO_x$) present in the supplied gas or gas mixture is reduced to $N_2$ through a selective catalytic reaction. Downstream of SCR catalytic converter 12, the emerging gas 5" is then conveyed further and removed.

Emerging gas 5", as pollutant components, now has only $NO_x$, in the event the supply of ammonia via the second gas supply device was not sufficient (insufficient emission reduction), or $NH_3$, in the event the supply of ammonia was too great ($NH_3$ emission or $NH_3$ breakthrough). Further oxidizable gas components, such as CO and HC, were already removed from supplied gas 5 by oxidation catalytic converter 10.

Therefore, in order to check quantitatively whether the $NH_3$ supplied is adequate, too great, or too small, a gas sensor 15 is provided downstream of SCR catalytic converter 12, the gas sensor being sensitive in a non-selective manner, or across a broad spectrum, with respect to oxidizable gas components and being in contact with emerging gas 5". Gas sensor 15 is, for example, an available gas sensor having metallic electrodes on a Pt/Au base, which are widely used as HC sensors. Sensors of this type have a logarithmic characteristic curve as a function of the gas concentration, i.e., they have a very high sensitivity especially in the range of concentrations under 100 ppm, such as may arise in an $NH_3$ breakthrough, and therefore they make possible, in a very effective and simple manner, a quantitative determination of the oxidizable gas components in emerging gas 5".

Furthermore, gas sensor 15 is connected to an available processing unit 16 for receiving, evaluating, and conditioning the signals of gas sensor 15. Processing unit 16 is also connected to a control unit 17, which via a control line 18 is connected to dosing system 13. In this context, processing unit 16, control unit 17, control line 18 and dosing system 13, or the second gas supply device, are also integrated in one assembly.

Therefore, via control unit 17, as a function of the measuring signal of gas sensor 15, it is possible to control the ammonia supply to substantially oxidized gas 5' before it enters into SCR catalytic converter 12, the ammonia supply in an available manner always being regulated in the form of a closed feedback circuit, such that, on the one hand, the most complete reduction possible and therefore the removal of nitrogen oxide from the emerging gas 5" is achieved, and that, on the other hand, at the same time the smallest possible amount of ammonia is contained in the emerging gas 5".

What is claimed is:

1. A device for detecting at least one of ammonia and an NH3 slip emission, in a catalytic converter arrangement having an SCR catalytic converter, the device comprising:
   a first gas supply device for supplying an exhaust gas of an internal combustion engine to the SCR catalytic converter;
   a second gas supply device for supplying at least one of the ammonia and the NH3 slip emission to the SCR catalytic converter;
   an arrangement for at least substantially oxidizing oxidizable gas components of the exhaust gas, prior to the exhaust gas being supplied to the SCR catalytic converter, for providing at least a substantially oxidized gas; and
   an arrangement for analyzing an emerging gas from the SCR catalytic converter with respect to the oxidizable gas components, wherein the arrangement for analyzing the emerging gas does not react selectively to specific oxidizable gases.

2. The device of claim 1, wherein the arrangement for at least substantially oxidizing includes an oxidation catalytic converter.

3. The device of claim 1, wherein the arrangement for analyzing includes a gas sensor.

4. The device of claim 1, wherein the second gas supply device includes a hydrolysis catalytic converter, a dosing system and a supply line.

5. The device of claim 4, wherein at least one of a chemical compound and urea is suppliable to the hydrolysis catalytic converter via the dosing system and the supply line.

6. The device of claim 5, wherein the at least one of the ammonia and the $NH_3$ slip emission is releasable from the at least one of the chemical compound and the urea in the hydrolysis catalytic converter.

7. The device of claim 1, wherein the first gas supply device initially supplies the at least a substantially oxidized gas, which is suppliable to the SCR catalytic converter, to the second gas supply device.

8. The device of claim 7, wherein, in the second gas supply device, the at least one of the ammonia and the $NH_3$ slip emission suppliable to the SCR catalytic converter is mixable with the at least a substantially oxidized gas, which is suppliable via the first gas supply device to the SCR catalytic converter.

9. The device of claim 1, wherein the arrangement for analyzing include a gas sensor and is coupled to a processing unit, which is coupled to the second gas supply device via a control unit and a control line.

10. The device of claim 9, wherein the processing unit, the control unit, and the second gas supply device are integrated in one assembly.

11. The device of claim 9, wherein the arrangement for analyzing provides a measuring signal for the second gas supply device to regulate a supplied quantity of the at least one of the ammonia and the $NH_3$ slip emission.

12. The device of claim 1, wherein the device is used for at least one of detecting and minimizing the at least one of the ammonia and the $NH_3$ slip emission in the catalytic converter arrangement for reducing $NO_x$ emissions from an internal combustion engine.

13. A method for detecting at least one of ammonia and an NH3 slip emission in a catalytic converter arrangement having an SCR catalytic converter, the method comprising the steps of:

supplying an exhaust gas of an internal combustion engine via a first gas supply device and the at least one of the ammonia and the NH3 slip emission via a second gas supply device to the SCR catalytic converter;

initially at least substantially oxidizing oxidizable gas components of the exhaust gas prior to supplying the exhaust gas to the SCR catalytic converter; and analyzing emerging gas from the SCR catalytic converter with respect to the oxidizable gas components, wherein the analyzing is performed by an arrangement that does not react selectively to specific oxidizable gases.

14. The method of claim 13, wherein an oxidation catalytic converter performs the step of at least substantially oxidizing the oxidizable gas components of the exhaust gas prior to its being supplied to the SCR catalytic converter.

15. The method of claim 13, wherein the gas sensor is coupled to the second gas supply device, which is regulated with respect to a quantity of the at least one of the ammonia and the $NH_3$ slip emission and supplied to the SCR catalytic converter to minimize a concentration of the oxidizable gas components of the emerging gas from the SCR catalytic converter.

16. The method of claim 13, wherein the method is used for at least one of detecting and minimizing the at least one of the ammonia and the $NH_3$ slip emission in the catalytic converter arrangement for reducing $NO_x$ emissions from an internal combustion engine.

\* \* \* \* \*

UNITED STATES PATENT AND TRADEMARK OFFICE
CERTIFICATE OF CORRECTION

PATENT NO. : 6,625,975 B1
DATED : September 30, 2003
INVENTOR(S) : Roland Stahl et al.

It is certified that error appears in the above-identified patent and that said Letters Patent is hereby corrected as shown below:

Column 1,
Lines 33-34, change "sensor by be required" to -- sensor is may be required. --

Column 2,
Line 60, change "No. 0800 856," to -- No. 0 800 856 --

Column 3,
Line 67, change "an available gas sensor" to -- an available known gas sensor --

Signed and Sealed this

Third Day of May, 2005

JON W. DUDAS
*Director of the United States Patent and Trademark Office*